(12) United States Patent
Nanko et al.

(10) Patent No.: US 7,323,687 B2
(45) Date of Patent: Jan. 29, 2008

(54) INFRARED GAS ANALYZER AND INFRARED GAS ANALYSIS METHOD

(75) Inventors: Tomoaki Nanko, Musashino (JP); Hideaki Yamagishi, Musashino (JP); Shigeru Matsumura, Masashino (JP)

(73) Assignee: Yokogawa Electric Corporation, Musashino-shi, Tokyo (JP)

( * ) Notice: Subject to any disclaimer, the term of this patent is extended or adjusted under 35 U.S.C. 154(b) by 175 days.

(21) Appl. No.: 11/232,657

(22) Filed: Sep. 22, 2005

(65) Prior Publication Data
US 2006/0118724 A1 Jun. 8, 2006

(30) Foreign Application Priority Data
Oct. 26, 2004 (JP) ............................ 2004-310722

(51) Int. Cl.
*G01J 5/02* (2006.01)
*G01N 21/61* (2006.01)
(52) U.S. Cl. ................................. 250/343; 250/339.13
(58) Field of Classification Search ........... 250/339.13, 250/343
See application file for complete search history.

(56) References Cited

U.S. PATENT DOCUMENTS

| | | | |
|---|---|---|---|
| 3,180,984 A * | 4/1965 | Fertig et al. | 250/341.7 |
| 3,560,735 A | 2/1971 | Strange et al. | |
| 3,731,092 A * | 5/1973 | Freilino | 250/346 |
| 4,180,733 A | 12/1979 | Ueda | |
| 4,271,124 A * | 6/1981 | Speeter | 250/343 |
| 4,885,469 A | 12/1989 | Yamagishi et al. | |
| 5,332,901 A * | 7/1994 | Eckles et al. | 250/345 |
| 5,572,032 A * | 11/1996 | Fujiwara et al. | 250/345 |
| 5,764,354 A * | 6/1998 | Aidam et al. | 250/343 |

(Continued)

FOREIGN PATENT DOCUMENTS

GB    1 276 194    6/1972

(Continued)

*Primary Examiner*—David Porta
*Assistant Examiner*—Mindy Vu
(74) *Attorney, Agent, or Firm*—Flynn, Thiel, Bouiel & Tanis, P.C.

(57) ABSTRACT

There are provided an infrared gas analyzer of a simple configuration, capable of taking measurements with high precision when using an infrared light source excellent in thermal responsiveness, and capable of ON/OFF operations at high speed, and an infrared gas analysis method using the same. The infrared gas analyzer having a sample cell into which a sample gas is distributed, for detecting concentration of a measuring target component of the sample gas by taking advantage of variation in absorption amount of infrared rays having passed through the sample cell, comprising a first infrared light source for irradiating the sample cell with first infrared rays, a second infrared light source having a response characteristic equal to that of the first infrared light source, a detector for detecting a difference between the first infrared rays emitted from the first infrared light source, and having passed through the sample cell, and second infrared rays emitted from the second infrared light source, a light source drive controller for synchronously driving the first and second infrared light sources, respectively, and a measurement controller for providing the light source drive controller with instructions for respective drive amounts of the first and second infrared light sources while receiving an output signal from the detector, thereby generating a measurement output corresponding to the concentration of the measuring target component of the sample gas.

20 Claims, 8 Drawing Sheets

U.S. PATENT DOCUMENTS 5,818,598 A * 10/1998 Kebabian .................... 356/437
6,452,182 B1 * 9/2002 Zochbauer et al. ......... 250/344

FOREIGN PATENT DOCUMENTS

| GB | 2 218 804 | 11/1989 |
| JP | 3174069 | 3/2001 |
| JP | 2001-221737 | 8/2001 |
| JP | 2002-131230 | 5/2002 |

* cited by examiner

INFRARED GAS ANALYZER AND INFRARED GAS ANALYSIS METHOD

FIELD OF THE INVENTION

The invention relates to an infrared gas analyzer for detecting concentration of a measuring target component of a sample gas by taking advantage of infrared light ray absorption characteristics of a measuring target gas, and an infrared gas analysis method using the same.

More specifically, the invention is concerned with an infrared gas analyzer capable of executing high-precision measurements with a simple configuration in the case of using light sources excellent in thermal responsiveness, and capable of executing ON/OFF operations at high speed as infrared light sources, and an infrared gas analysis method using the same.

BACKGROUND OF THE INVENTION

FIG. 7 is a block diagram showing an example of a conventional infrared gas analyzer. As shown in the figure, infrared light rays emitted from an infrared light source 1 are divided into two infrared light components by a distribution cell 2 to thereby enter a reference cell 3, and a sample cell 4, respectively. A gas not containing a measuring target component, such as an inert gas, and so forth, is sealed in the reference cell 3. A sample gas is distributed into the sample cell 4. As a result, only one of the two infrared light components of the infrared light rays, after divided by the distribution cell 2, on the side of the sample cell 4, is subjected to absorption by the measuring target component, subsequently reaching a detector 5.

The detector 5 has two chambers consisting of a reference side chamber 51 for receiving the infrared light component from the reference cell 3, and a sample side chamber 52 for receiving the other infrared light component from the sample cell 4, and a flow sensor 53 for detecting gas flow is provided in a gas distribution path linking the two chambers with each other. Further, a gas containing the same component as the measuring target component is sealed in the detector 5, and upon the respective infrared light components from the reference cell 3, and the sample cell 4, falling on the detector 5, the measuring target component of the gas, as sealed, absorbs the infrared light component, whereupon the respective gases inside the reference side chamber 51 and the sample side chamber 52 undergo thermal expansion.

Since a reference gas inside the reference cell 3 does not contain the measuring target component, there occurs no absorption of the infrared light component passing through the reference cell 3 by the measuring target component, and if the measuring target component is contained in the sample gas inside the sample cell 4, portions of the infrared light component are absorbed, thereby resulting in a decease in quantity of the infrared light component, falling on the sample side chamber 52 of the detector 5, so that thermal expansion of the gas inside the reference side chamber 51 becomes larger than thermal expansion of the gas in the sample-side chamber 52. The infrared light rays are interrupted by a rotary sector 6, the rotary sector 6 repeating blockage and irradiation, and when the infrared light rays are cut off, the infrared light component falls on neither the reference side chamber 51 nor the sample side chamber 52, so that the gases do not expand.

Consequently, there occurs a pressure difference according to the concentration of the measuring target component of the sample gas, periodically between the reference side chamber 51 and the sample side chamber 52, thereby causing the gases to come and go through the gas distribution path provided between both the chambers. Behavior of the gases is detected by the flow sensor 53 to be subsequently amplified at an AC voltage by a signal processing circuit 7, thereby outputting a signal corresponding to the concentration of measuring target component. Reference numeral 8 denotes a synchronous motor for driving the rotary sector 6, and 9 a trimmer for adjusting balance between the infrared light components falling on the reference cell 3, and the sample cell 4, respectively.

Thus, if the concentration of the measuring target component of the sample gas undergoes a change, there occurs a change in quantity of the infrared light component falling on the detector 5 (the sample side chamber 52), so that it is possible to obtain an output signal corresponding to the concentration of the measuring target component via the signal processing circuit 7.

With the conventional infrared gas analyzer as shown in FIG. 7, for the infrared light source 1, use is made of a ceramic heater, and so forth, with a configuration for overcoming various problems, such as poor thermal responsiveness at the light source, fluctuation, drift, and so on, of the light source.

That is, while the rotary sector is in use for turning the infrared light rays ON/OFF, the infrared light rays emitted from a common light source are divided into the two infrared light components before falling on the sample cell and the reference cell, respectively, in order to eliminate effects of light source variation.

FIG. 8 is a block diagram showing an example of an infrared light source excellent in thermal responsiveness. FIG. 8A is a plan view, and FIG. 8B is a sectional view taken on line A-A in FIG. 8A. As shown in the figures, an infrared light source 1 is structured such that a filament 12 in a micro-bridge-like shape is supported above a recess 11 formed in a silicon substrate 10.

The filament 12 has its plane shape formed by forming a polycrystalline silicon layer 14 highly doped with boron on top of a silicon dioxide film 13 formed on a silicon substrate 10, and subsequently, by applying linear patterning to the polycrystalline silicon layer 14.

Then, a portion of the silicon substrate 10, below the filament 12, is removed by anisotropic differential concentration etching using the silicon dioxide film 13 formed on both the top and bottom faces of the silicon substrate 10, respectively, as masks, thereby forming the recess 11, whereupon there is implemented a micro-bridge structure for supporting the filament 12 linear in shape, above the recess 11.

Subsequently, portions of a silicon dioxide film 15 formed on the polycrystalline silicon layer 14 are removed to form electrodes 16a, 16b, and current is supplied to the filament 12 via the electrodes 16a, 16b, thereby causing the filament 12 to generate heat to emit infrared rays corresponding to a heat generation temperature.

The infrared light source 1 as described is excellent in thermal responsiveness and high in emissivity of the infrared rays while ON/OFF thereof at high speed is possible, thereby being driven with a simple drive circuit. Further, as a semiconductor process is utilized in manufacturing the same, it is possible to manufacture high-performance infrared light sources having uniform properties at a low cost on a mass production basis.

[Patent Document 1] JP-A No. 131230/2002
[Patent Document 2] JP-B No. 3174069
[Patent Document 3] JP-A No. 221737/2001

SUMMARY OF THE INVENTION

However, if the infrared light source described as above, is used for an analyzer of the conventional configuration as shown in FIG. 7, unnecessary constituent members are too many in view of the nature of the infrared light source, so that it is not possible to fully get the advantage of the light source.

Further, there have never been proposed a configuration of an analyzer suitable for use of the infrared light source described, and a measuring method using the same.

It is therefore an object of the invention to eliminate shortcomings of the conventional infrared gas analyzer, as described in the foregoing, and to implement an infrared gas analyzer of a simple configuration, capable of taking measurements with high precision when using the infrared light source excellent in thermal responsiveness, and capable of ON/OFF operations at high speed, and an infrared gas analysis method using the same.

To achieve the above object, it is a first aspect of the invention to provide an infrared gas analyzer having a sample cell into which a sample gas is distributed, for detecting concentration of a measuring target component of the sample gas by taking advantage of variation in absorption amount of infrared rays having passed through the sample cell, wherein the infrared gas analyzer comprises a first infrared light source for irradiating the sample cell with infrared rays, a second infrared light source having a response characteristic equal to that of the first infrared light source, a detector for detecting a difference between the first infrared rays emitted from the first infrared light source, and having passed through the sample cell, and second infrared rays emitted from the second infrared light source, a light source drive controller for synchronously driving the first and second infrared light sources, respectively, and a measurement controller for providing the light source drive controller with instructions for respective drive amounts of the first and second infrared light sources while receiving an output signal from the detector, thereby generating a measurement output corresponding to the concentration of the measuring target component of the sample gas.

It is a second aspect of the invention to provide an infrared gas analysis method of detecting concentration of a measuring target component of a sample gas by taking advantage of variation in absorption amount of infrared rays having passed through a sample cell into which the sample gas is distributed, wherein the infrared gas analysis method comprises the steps of irradiating the sample cell with first infrared rays emitted from a first infrared light source, irradiating a balance side chamber with second infrared rays emitted from a second infrared light source having a response characteristic equal to that of the first infrared light source, synchronously driving the first and second infrared light sources while detecting a difference between the first infrared rays having passed through the sample cell, and the second infrared rays, and generating a measurement output corresponding to the concentration of the measuring target component of the sample gas.

Thus, with adoption of a configuration where the first infrared light source for irradiating the sample cell with the first infrared rays, and the second infrared light source having the response characteristic equal to that of the first infrared light source are provided, the first and second infrared light sources are synchronously driven while the difference between the first infrared rays having passed through the sample cell and the second infrared rays is detected, thereby generating the measurement output corresponding to the concentration of the measuring target component of the sample gas, the reference cell and the rotary sector are no longer required, so that it becomes possible to implement the infrared gas analyzer of the simple configuration, capable of taking measurements with high precision when using the infrared light source excellent in thermal responsiveness, and capable of ON/OFF operations at high speed, and the infrared gas analysis method using the same.

Further, if the drive amount of the second infrared light source is controlled such that the output of the detector at the time of the measuring operation becomes always zero to thereby obtain the measurement output on the basis of the drive amount differential, this will enable the detector to be always used in a range where an output signal thereof remains small in value, thereby widening a dynamic range of a measurement range thereof.

PREFERRED EMBODIMENTS OF THE INVENTION

An infrared gas analyzer and an infrared gas analysis method using the same, according to the invention, are described hereinafter with reference to the accompanying drawings.

Embodiment 1

Figure 1:
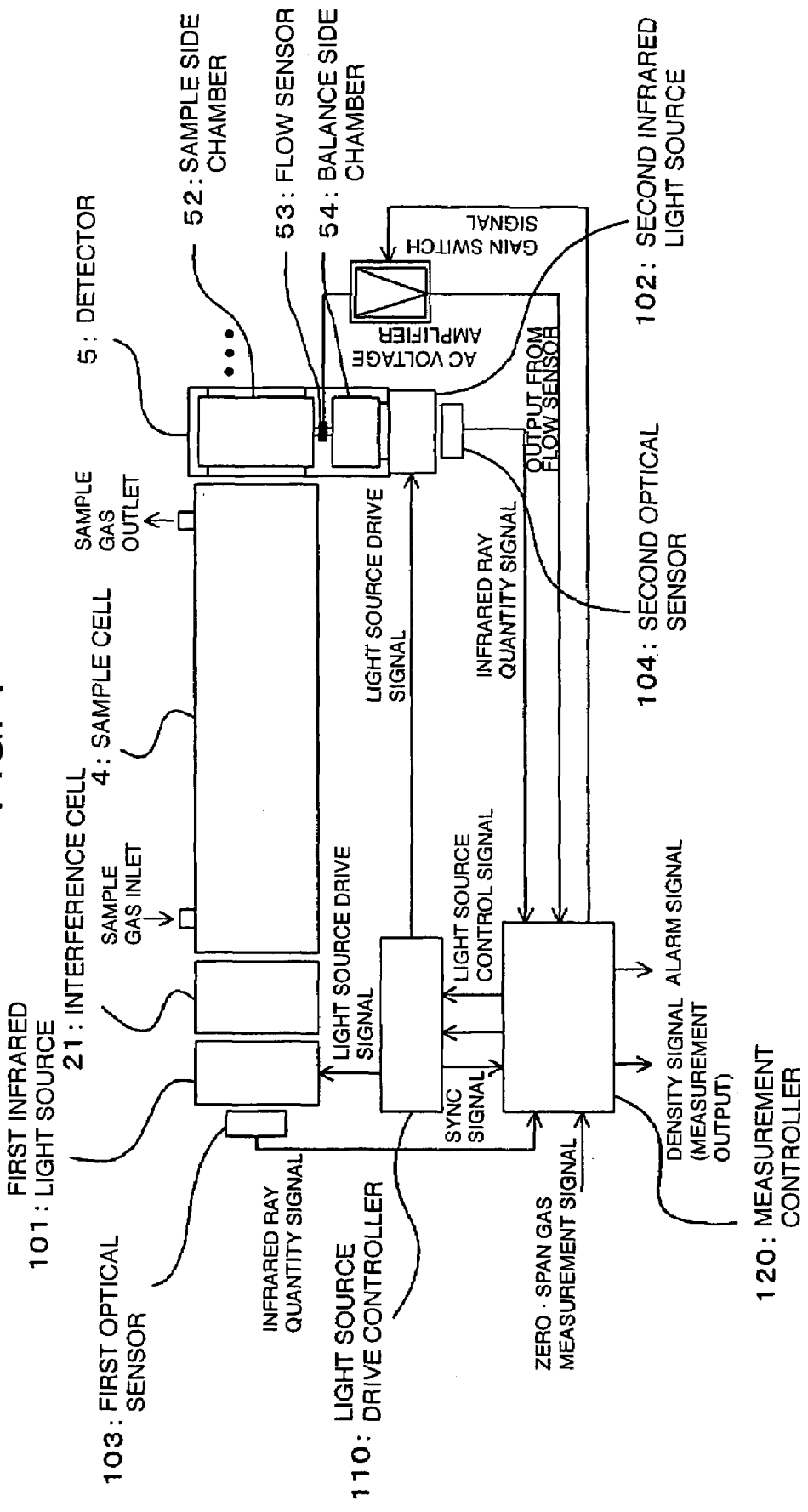
FIG. 1 is a block diagram showing one embodiment of an infrared gas analyzer, and an infrared gas analysis method using the same, according to the invention.
Figure 7:
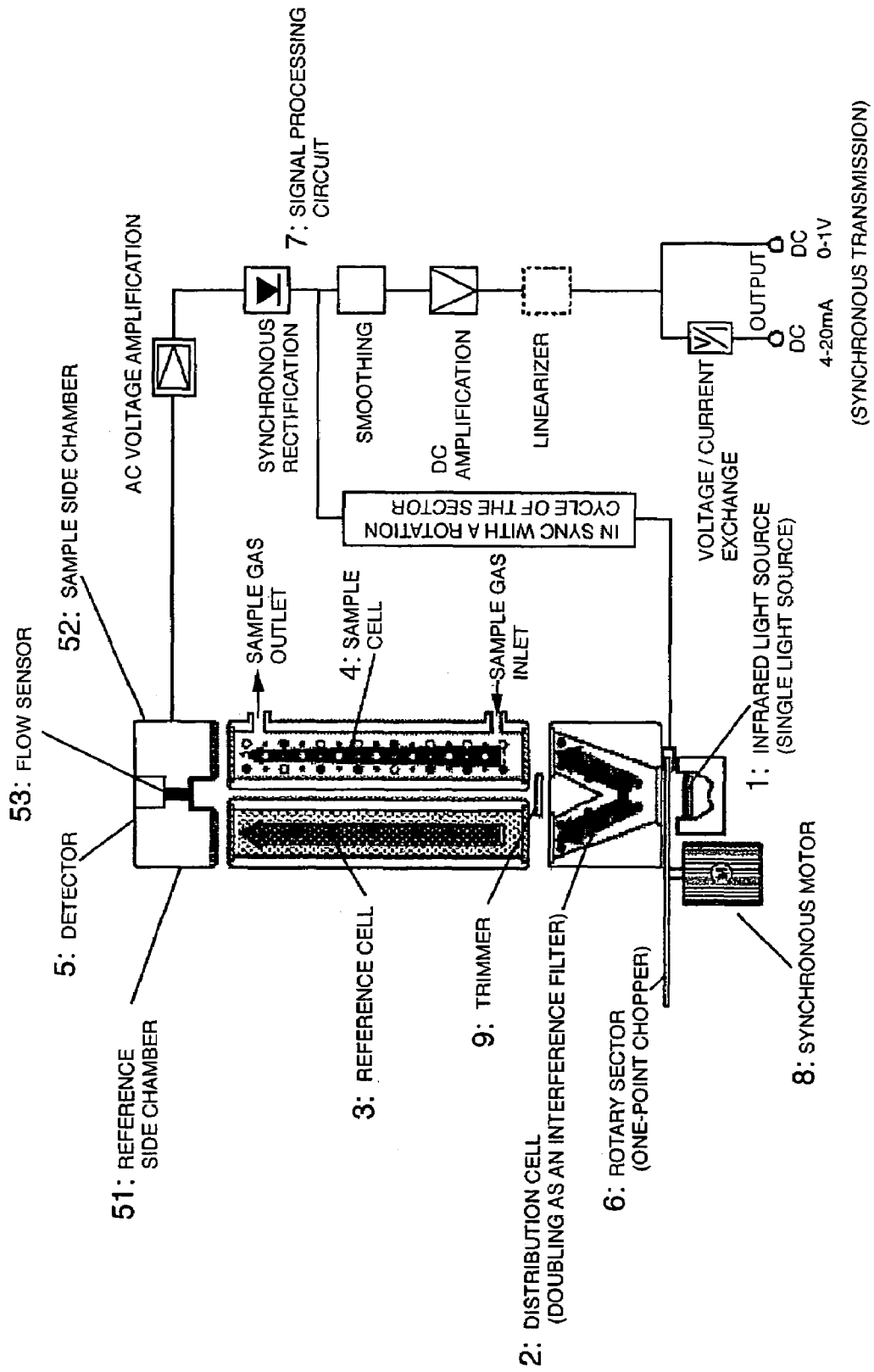
FIG. 7 is a block diagram showing an example of a conventional infrared gas analyzer.
Figure 8A:
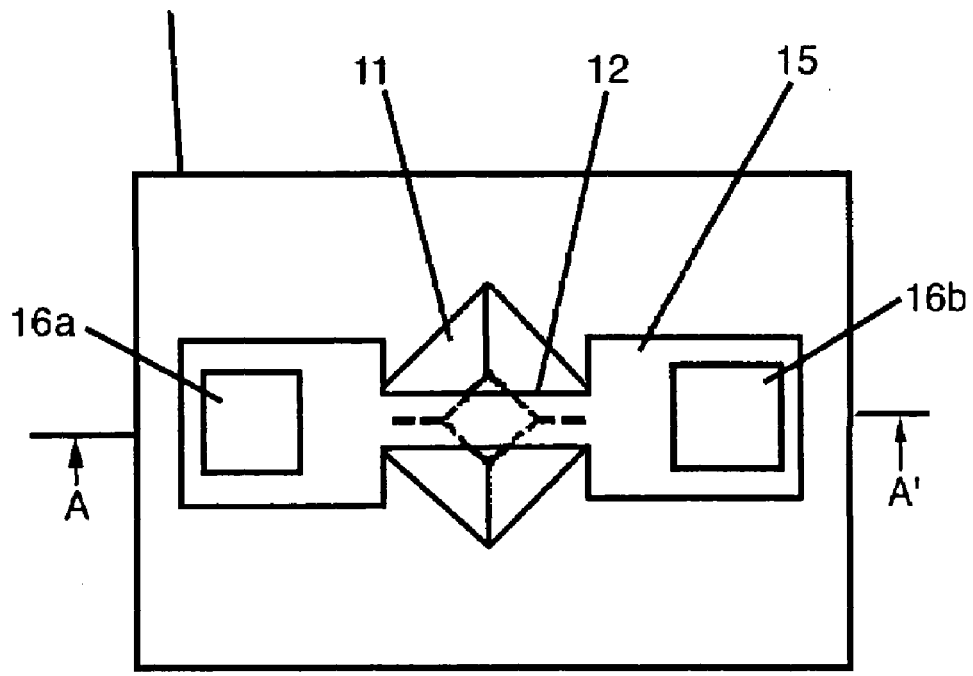
FIG. 8 is a block diagram showing an example of an infrared light source excellent in thermal responsiveness.
Figure 8B:
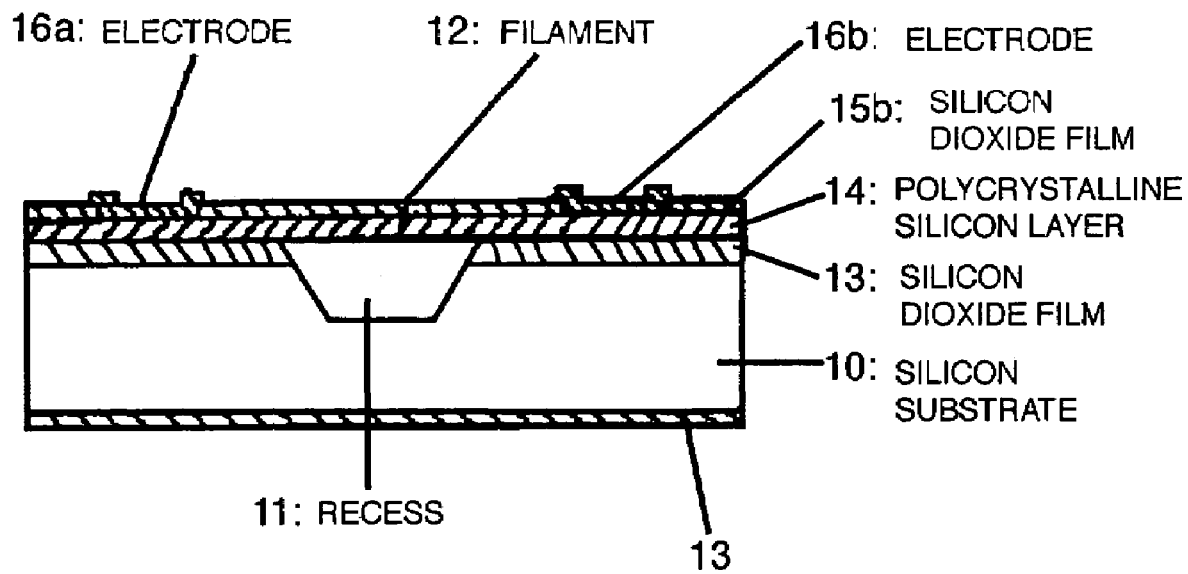

FIG. 1 is a block diagram showing one embodiment of an infrared gas analyzer, and an infrared gas analysis method using the same, according to the invention. In the figure, parts corresponding to those in FIG. 7 are denoted by like reference numerals. Reference numerals 101, 102 denote first and second infrared light sources, respectively, excellent in thermal responsiveness, such as one previously described with reference to FIG. 8, and the first infrared light source 101 irradiates a sample cell 4 with first infrared rays via an interference cell 21. Further, the second infrared light source 102 irradiates a balance side chamber 54 of a detector 5 with second infrared rays. In this case, the detector 5 has the balance side chamber 54 for receiving the second infrared rays, in place of the conventional reference side chamber 51, and a flow sensor 53 is provided in a gas distribution path linking a sample side chamber 52 for receiving the first infrared rays via the sample cell 4 with the balance side chamber 54. Consequently, the detector 5 detects a difference between the first infrared rays passing through the sample cell 4, and the second infrared rays falling directly on the detector 5 from the second infrared light source 102. Further, for each of the first and second infrared light sources 101, 102, use is made of an infrared light source having identical responsiveness.

Reference numerals 103, 104 denote first and second optical sensors, respectively, for detecting respective quantities of infrared rays emitted from the first and second infrared light sources 101, 102, respectively, reference numeral 110 denotes a light source drive controller for generating light source drive signals to thereby synchronously drive the first and second infrared light sources 101, 102, and 120 denotes a measurement controller for providing the light source drive controller 110 with instructions for respective drive amounts of the first and second infrared light sources 101, 102 as the light source control signals, and generating a measurement output corresponding to concentration of a measuring target component of a sample gas after receiving an output signal from the detector 5 (the flow sensor 53).

The light source drive controller 110 drives the first and second infrared light sources 101, 102 according to the light source drive signal composed of, for example, rectangular waves propagating in a predetermined cycle, thereby synchronously turning ON/OFF the first and second infrared light sources 101, 102. Consequently, when the first and second infrared light sources 101, 102 are lit up, a differential pressure corresponding to a difference between the first infrared rays, and the second infrared rays is developed between the respective chambers of the detector 5 while when the first and second infrared light sources 101, 102 are put out, a differential pressure is not developed. Consequently, the flow sensor 53 generates an output corresponding to the concentration of the measuring target component of the sample gas.

The measurement controller 120 executes synchronous rectification of the output of the flow sensor 53 by utilizing the drive signal (synchronous signal) for the first and second infrared light sources 101, 102, thereby outputting a measurement output corresponding to the concentration of the measuring target component of the sample gas.

Hereinafter, there will be sequentially described control of the respective drive amounts of the first and second infrared light sources 101, 102, by the measurement controller 120.

With an infrared gas analyzer, it is a general practice to conduct calibration operations, such as zero adjustment, span adjustment, and so forth, prior to a measuring operation. At the time of the zero adjustment operation for distributing a reference gas (zero gas) that does not contain the measuring target component into the sample cell 4, the drive amount of the first infrared light source 101 is adjusted to a value suited for measurement while adjusting the drive amount of the second infrared light source 102 such that the output signal from the detector 5 (the flow sensor 53) becomes zero. Meanwhile, at the time of the span adjustment operation for distributing a reference gas (span gas) with a known concentration of the component into the sample cell 4, a gain, and so forth of a measurement circuit are adjusted such that the measurement output indicates a predetermined concentration value.

Next, at the time of the measuring operation for distributing the sample gas into the sample cell 4, the measurement controller 120 receives the output signal from the detector 5 (the flow sensor 53), whereupon a measurement output corresponding to the concentration of the measuring target component of the sample gas is generated.

Further, the measurement controller 120 receives respective outputs of the first and second optical sensors 103, 104, and generates an alarm signal in case that there occurs abnormality in the respective quantities of the infrared rays outgoing from the first and second infrared light sources 101, 102, respectively.

Thus, with adoption of the first and second infrared light sources 101, 102, excellent in thermal responsiveness, the infrared rays can be directly turned ON/OFF by the agency of the drive signal rectangular in waveform, so that the conventional rotary sector is no longer required. Furthermore, since the infrared light sources stable and having the identical responsiveness can be used, it is possible to cause infrared rays to directly fall on one (the balance side chamber 54) of photo-detection chambers of the detector 5, so that measurement with high precision can be implemented with the use of a simple configuration where the conventional reference cell is dispensed with.

Embodiment 2

Figure 2:
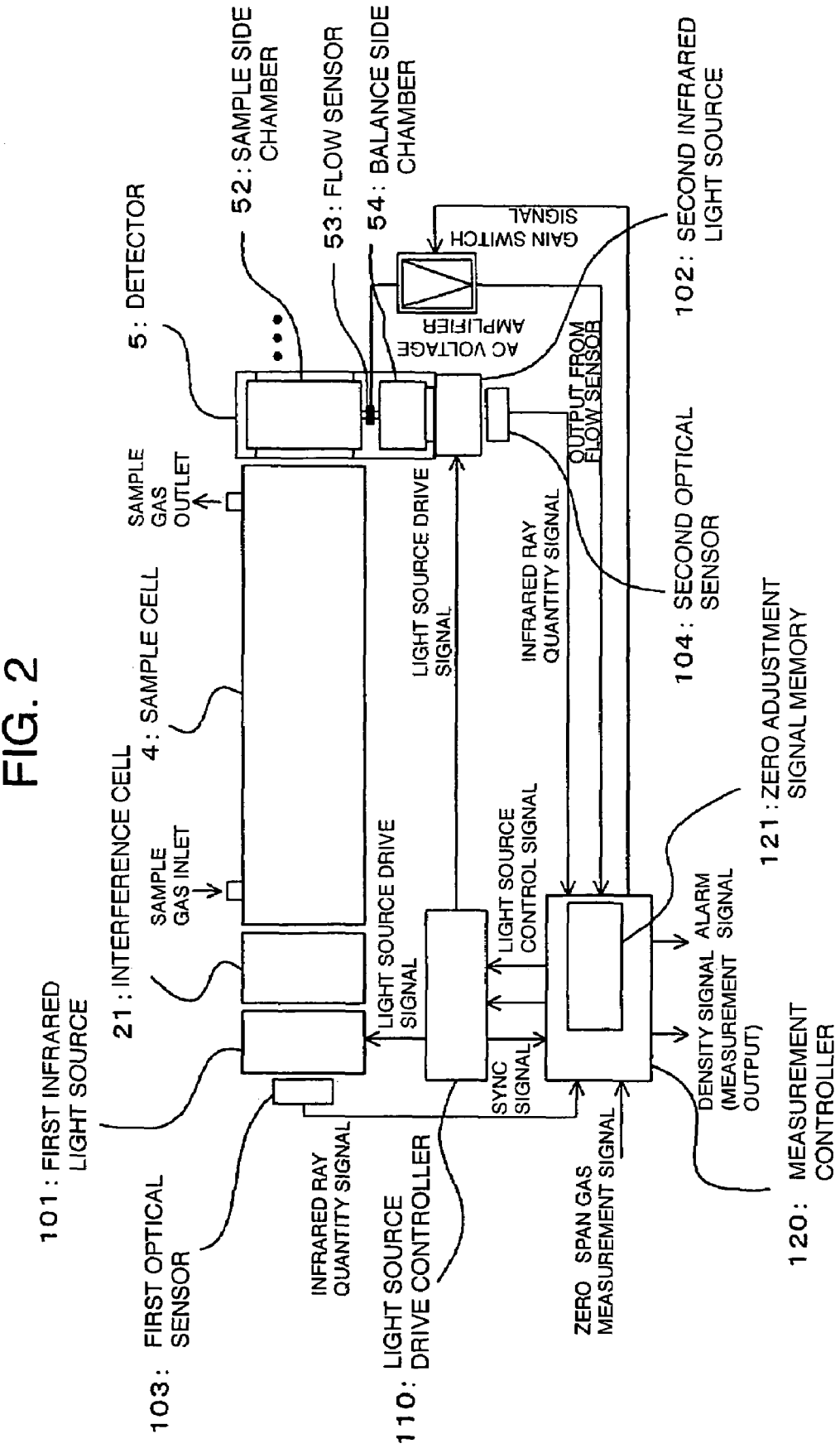
FIG. 2 is a block diagram showing another embodiment of an infrared gas analyzer, and an infrared gas analysis method using the same, according to the invention.

FIG. 2 is a block diagram showing another embodiment of an infrared gas analyzer, and an infrared gas analysis method using the same, according to the invention. In the figure, parts corresponding to those in FIG. 1 are denoted by like reference numerals. With the present embodiment shown in the figure, a drive amount of a second infrared light source 102 is adjusted at the time of a zero adjustment operation such that a difference between first infrared rays falling on a sample side chamber 52 of a detector 5, via a sample cell 4, and second infrared rays falling directly on a balance side chamber 54 from the second infrared light source 102 becomes zero, and an output of the detector 5 (a flow sensor 53) becomes zero while the drive amount of the second infrared light source 102 is adjusted at the time of a measuring operation as well such that the output of the detector 5 (flow sensor 53) becomes zero, thereby obtaining a measurement output corresponding to concentration of a measuring target component of a sample gas on the basis of a drive amount differential.

More specifically, a measurement controller 120 has a zero adjustment signal memory 121 for storing a drive amount of the second infrared light source 102, at the time of the zero adjustment operation, and detects a change in the second infrared rays, corresponding to the measuring target component, on the basis of the drive amount differential of the second infrared light source 102, at the time of the measuring operation.

Thus, if the drive amount of the second infrared light source 102 is controlled such that the output of the detector 5 (flow sensor 53) at the time of the measuring operation becomes always zero to thereby obtain the measurement output on the basis of the drive amount differential, this will enable the detector 5 (flow sensor 53) to be always used in a range where an output signal thereof remains small in value, thereby widening a dynamic range of a measurement range thereof.

Embodiment 3

Figure 3:
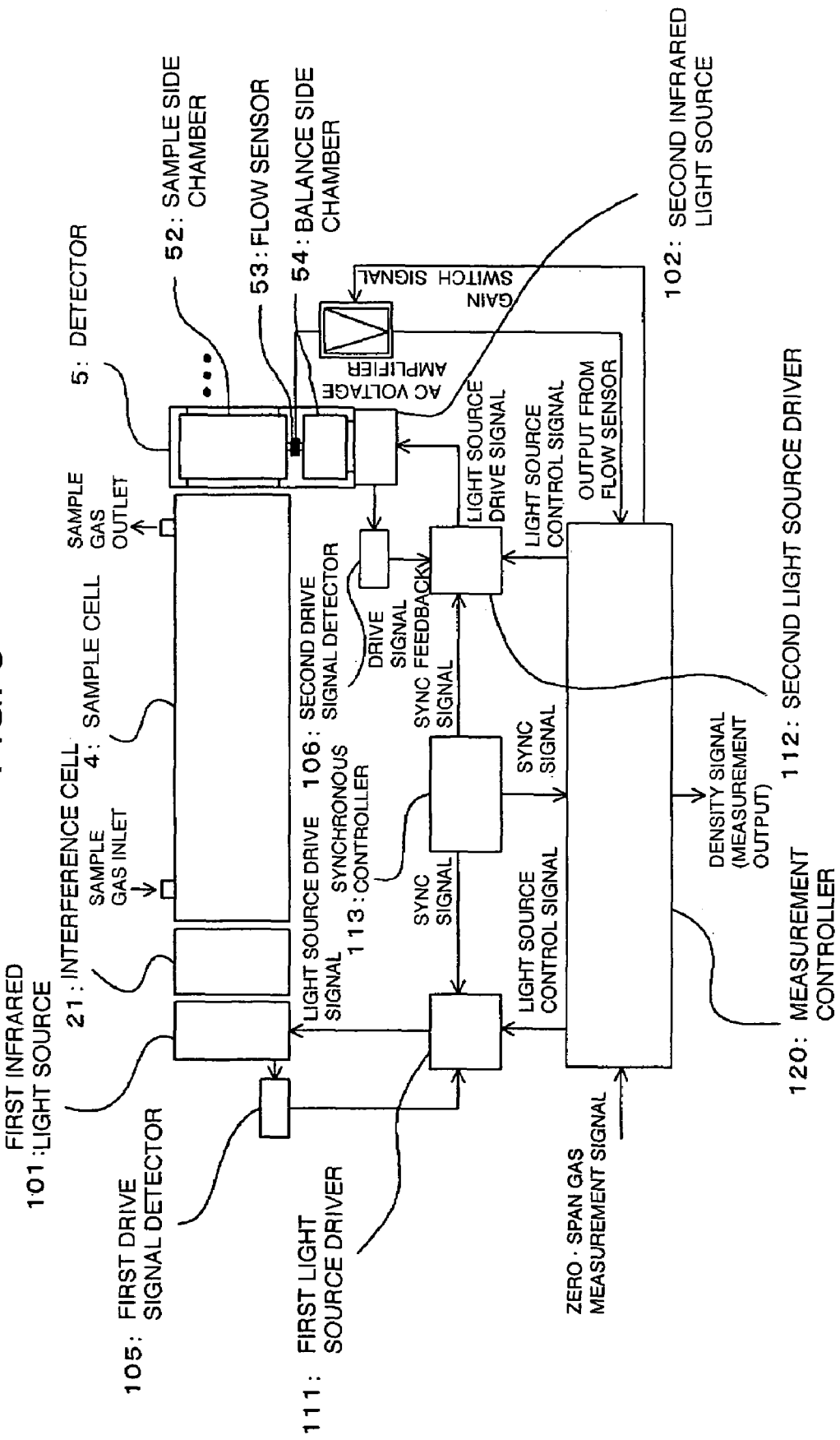
FIG. 3 is a block diagram showing still another embodiment of an infrared gas analyzer, and an infrared gas analysis method using the same, according to the invention.

FIG. 3 is a block diagram showing still another embodiment of an infrared gas analyzer, and an infrared gas analysis method using the same, according to the invention. In the figure, parts corresponding to those in FIG. 1 are denoted by like reference numerals. The present embodiment in the figure shows a specific configuration example of a light source drive controller 110 in FIG. 2 for driving first and second infrared light sources 101, 102, respectively. Reference numeral 113 denotes a synchronous controller for generating a sync signal rectangular in waveform, 111, 112 denote first and second light source drivers, respectively, for generating light source drive signals to be supplied to the first and second infrared light sources 101, 102, respectively, in response to the sync signal and light source control signals impressed from a measurement controller 120, and 105, 106 denote first and second drive signal detectors, respectively, for detecting the magnitudes of the respective light source drive signals to be supplied to the first and second infrared light sources 101, 102, and feeding back the same to the first and second light source drivers 111, 112, respectively.

That is, the magnitudes (voltages) of the respective light source drive signals to be supplied to the first and second infrared light sources 101, 102 are detected by the first and second drive signal detectors 105, 106, respectively, to be then fed back to the first and second light source drivers 111, 112, respectively, so that the first and second light source drivers 111, 112 are able to drive the first and second infrared light sources 101, 102, according to the respective light source drive signals of respective magnitudes corresponding to the light source control signals impressed by the measurement controller 120.

In general, a large current need be supplied in order to drive an infrared light source, and if the first and second light source drivers 111, 112 are poor in accuracy or resistance values of a cable, and so forth are subjected to an effect of a change in temperature, it is impossible to drive the infrared light sources with high precision owing to an effect of a change in resistance value, and so forth of a drive circuit. However, with adoption of the configuration shown in the figure, the first and second infrared light sources 101, 102 can be driven with high precision without being subjected to the effects described as above.

Further, the measurement controller 120 adjusts a drive amount of a second infrared light source 102 at the time of a zero adjustment operation such that a difference between first infrared rays falling on a sample side chamber 52 of a detector 5, via a sample cell 4, and second infrared rays falling directly on a balance side chamber 54 from the second infrared light source 102 becomes zero, and an output of the detector 5 (a flow sensor 53) becomes zero while receiving an output signal from the detector 5 (flow sensor 53) at the time of a measuring operation, thereby generating a measurement output corresponding to concentration of a measuring target component of a sample gas.

Embodiment 4

Figure 4:
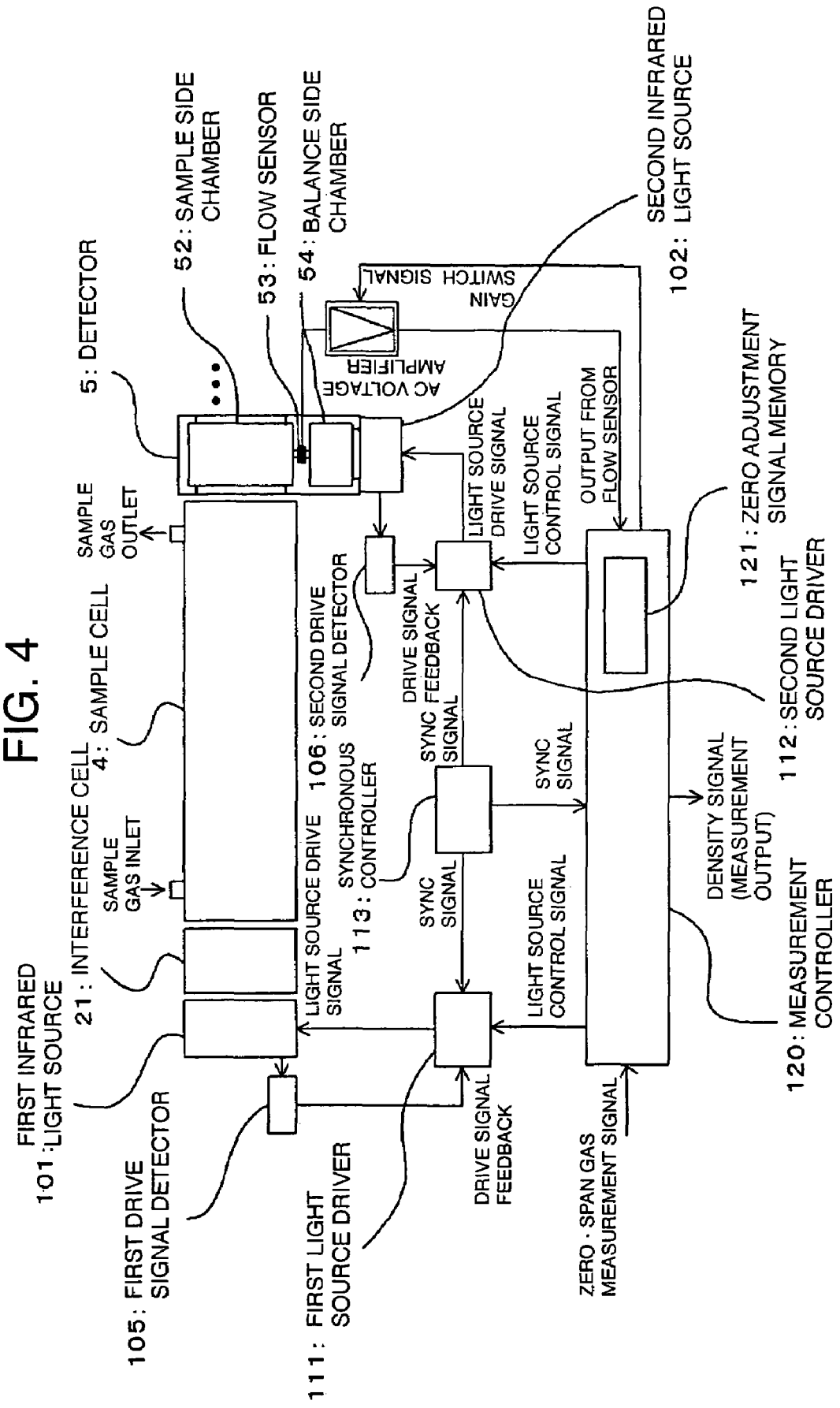
FIG. 4 is a block diagram showing a further embodiment of an infrared gas analyzer, and an infrared gas analysis method using the same, according to the invention.

FIG. 4 is a block diagram showing a further embodiment of an infrared gas analyzer, and an infrared gas analysis method using the same, according to the invention, In the figure, parts corresponding to those in FIGS. 2 and 3 are denoted by like reference numerals. The present embodiment shown in the figure is of the same configuration as that in FIG. 3, where the same measuring operation as described with reference to FIG. 2 is executed.

More specifically, a measurement controller 120 has a zero adjustment signal memory 121 for storing a drive amount of a second infrared light source 102, at the time of the zero adjustment operation, and a drive amount (a light source control signal) of the second infrared light source 102 is adjusted at the time of the zero adjustment operation such that a difference between first infrared rays falling on a sample side chamber 52 of a detector 5, via a sample cell 4, and second infrared rays falling directly on a balance side chamber 54 from the second infrared light source 102 becomes zero, and an output of the detector 5 (flow sensor 53) becomes zero while the drive amount of the second infrared light source 102 is adjusted at the time of a measuring operation as well such that the output of the detector 5 (flow sensor 53) becomes zero, thereby obtaining a measurement output corresponding to concentration of a measuring target component of a sample gas on the basis of a differential in the drive amount.

With the configuration described, the magnitude of a light source drive signal to be supplied to the second infrared light source 102 is detected by a second drive signal detector 106 to be then fed back to a second light source driver 112, however, in case of occurrence of a trouble, such as, for example, instability in operation for adjusting the drive amount, there may be a case where a feedback operation by the second drive signal detector 106 is omitted.

Embodiment 5

Figure 5:
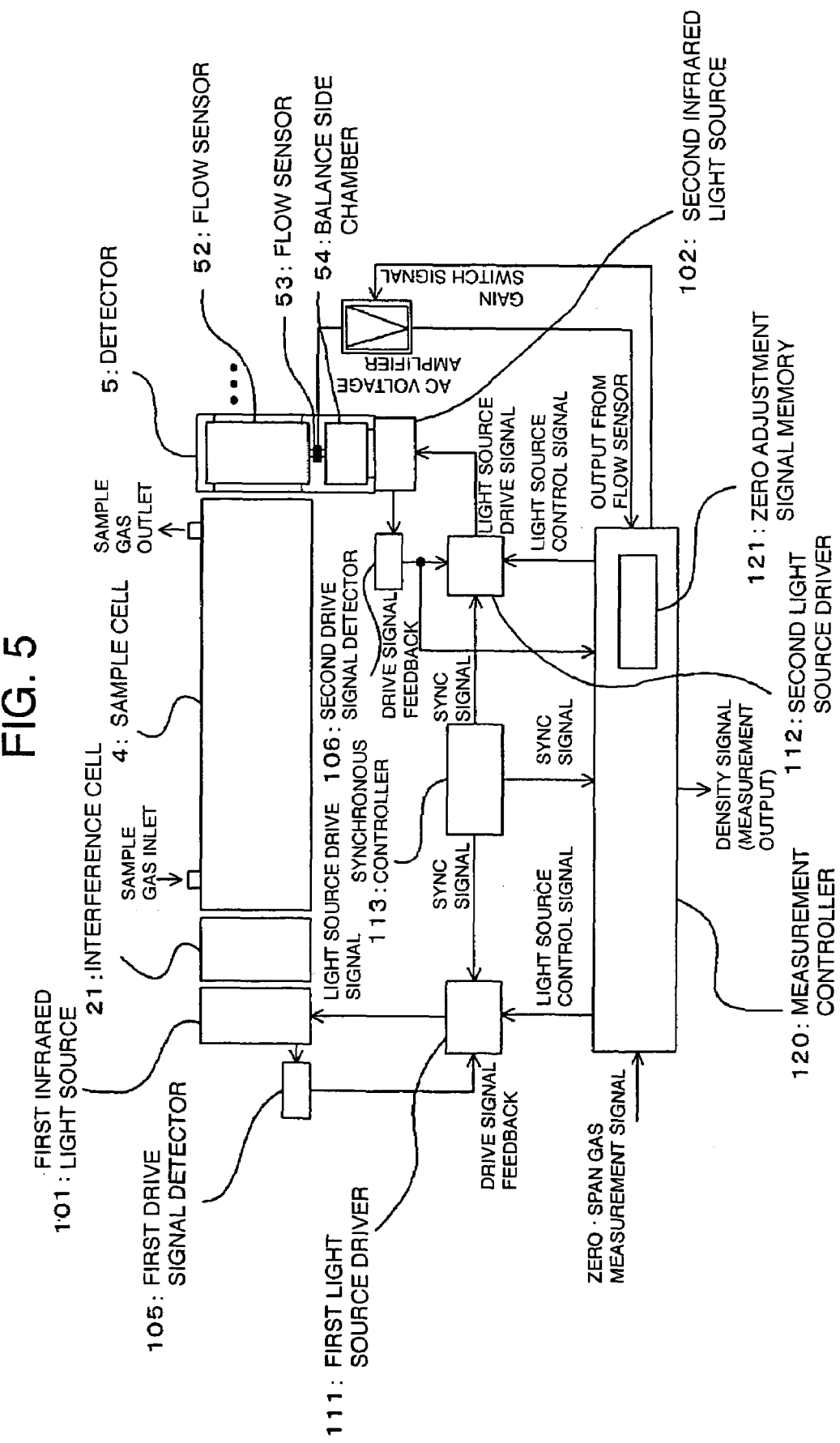
FIG. 5 is a block diagram showing a still further embodiment of an infrared gas analyzer, and an infrared gas analysis method using the same, according to the invention.

FIG. 5 is a block diagram showing a still further embodiment of an infrared gas analyzer, and an infrared gas analysis method using the same, according to the invention. In the figure, parts corresponding to those in FIG. 4 are denoted by like reference numerals. The present embodiment shown in the figure is of the same configuration as that in FIG. 4, where variation in drive amount of a second infrared light source 102 is obtained from an output of a second drive signal detector 106.

That is, if the drive amount of the second infrared light source 102 is obtained from the output of the second drive signal detector 106, this will enable an actual drive amount of the second infrared light source 102 to be accurately found, so that measurement with higher precision can be executed.

Embodiment 6

Figure 6:
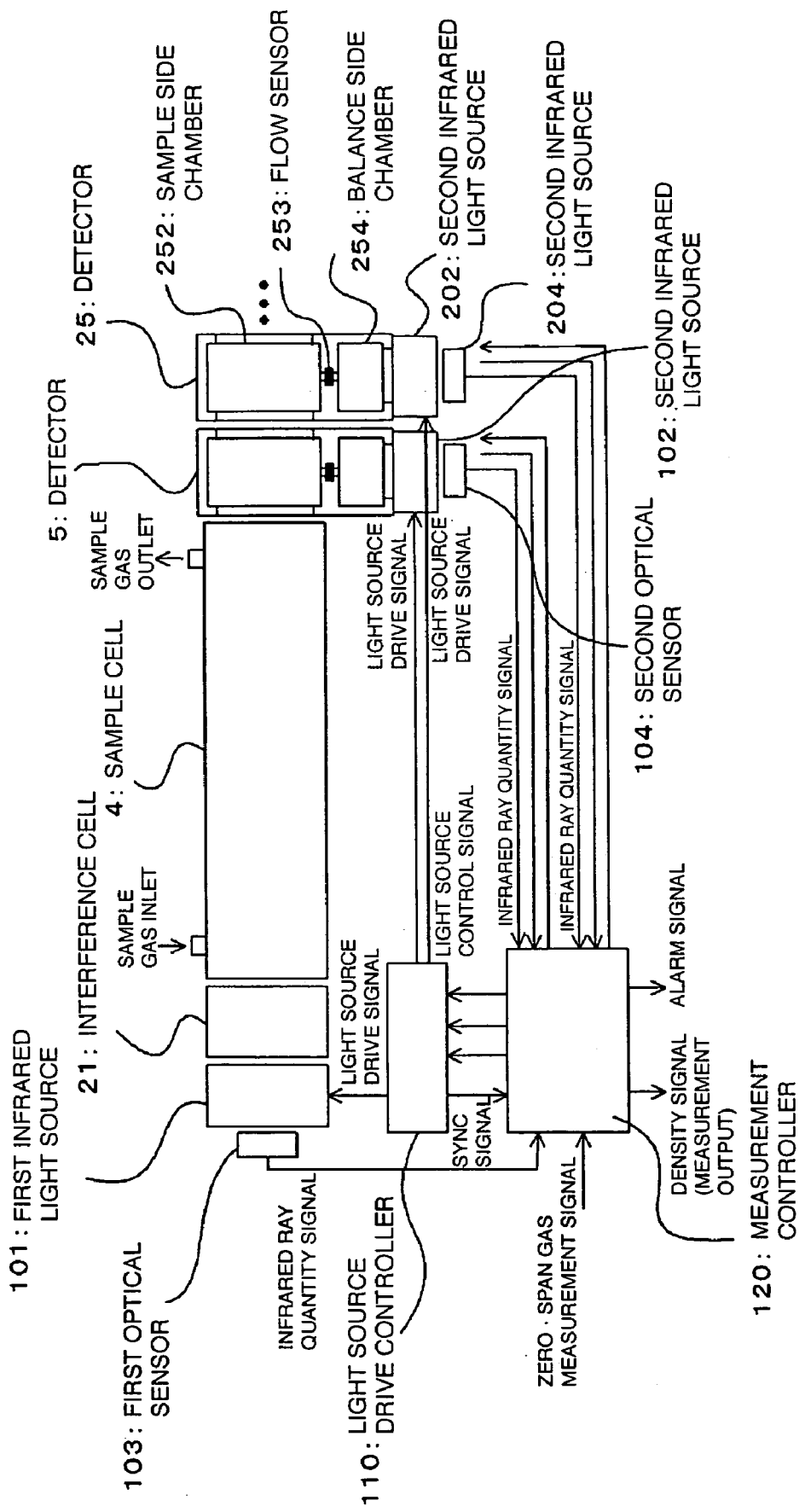
FIG. 6 is a block diagram showing a yet further embodiment of an infrared gas analyzer, and an infrared gas analysis method using the same, according to the invention.

FIG. 6 is a block diagram showing a yet further embodiment of an infrared gas analyzer, and an infrared gas analysis method using the same, according to the invention. In the figure, parts corresponding to those in FIG. 1 are denoted by like reference numerals. The present embodiment shown in the figure is of the same configuration as that in FIG. 1, where two detectors 5, 25 with gases differing in absorption characteristics from each other, sealed therein, respectively, are disposed in series, thereby enabling respective concentrations of two components of a sample gas to be concurrently measured.

More specifically, because first infrared rays passing through a sample side chamber 52 of a detector 5 are not subjected to absorption outside a wavelength region corresponding to a measuring target component gas sealed therein, so that with the use of a component gas having absorption characteristics in a wavelength region differing from the wavelength region described as above, it is possible to concurrently measure respective concentrations of two or a plurality of components.

A detector 25 is the same in configuration as the detector 5 and is comprised of a sample side chamber 252, a balance side chamber 254, and a flow sensor 253.

The first infrared rays emitted from a first infrared light source 101 passes through the sample side chamber 52 of the detector 5 after passing through a sample cell 4, and falls on the sample side chamber 252 of the detector 25. Further, the balance side chamber 254 is irradiated with second infrared rays from a second infrared light source 202.

An outgoing light quantity of the second infrared light source 202 is detected by a second optical sensor 204.

Further, in the figure, an AC amplifier for receiving an output of the flow sensor, and so forth are not shown.

An measuring operation on the side of the detector 25 is the same as the previously described measuring operation of the detector 5, and a second infrared light source 202 as well is turned ON/OFF in sync with the first and second infrared light sources 101, 102.

A measurement controller 120 independently controls respective drive amounts of the second infrared light sources 102, 202 to execute the same measuring operation as that described with reference to FIG. 1, for respective measuring target components (the detectors 5, 25).

In the foregoing description, there have been exhibited by way of example the case where the plurality of the components are concurrently measured with reference to the infrared gas analyzer of the configuration as shown in FIG. 1, and the infrared gas analysis method using the same, however, the configuration for the infrared gas analyzer, and the infrared gas analysis method, according to the invention, is not limited thereto, and with the configurations shown in FIGS. 2 to 5, respectively, similar measurement can be effected.

Furthermore, in the foregoing description, there have been exhibited by way of example the cases of driving the first and second infrared light sources 101, 102, and 202, respectively, by the drive signal rectangular in waveform, however, the drive signal is not limited thereto, and the drive signal may be trapezoidal in waveform.

What is claimed is:

1. An infrared gas analyzer having a sample cell into which a sample gas is distributed, for detecting the concentration of a measuring target component of the sample gas by taking advantage of a variation in an absorption amount of infrared rays having passed through the sample cell, said infrared gas analyzer comprising:
   a first infrared light source for irradiating the sample cell with infrared rays;
   a second infrared light source having a response characteristic equal to that of the first infrared light source;
   a detector for detecting a difference between the first infrared rays emitted from the first infrared light source and passed through the sample cell, and second infrared rays emitted from the second infrared light source and falling directly on the detector;
   a light source drive controller for synchronously driving the first and second infrared light sources, respectively; and
   a measurement controller for providing the light source drive controller with instructions for respective drive amounts of the first and second infrared light sources while receiving an output signal from the detector, thereby generating a measurement output corresponding to the concentration of the measuring target component of the sample gas.

2. An infrared gas analyzer according to claim 1, wherein the light source drive controller synchronously turns ON/OFF the first and second infrared light sources, respectively, in a predetermined cycle.

3. An infrared gas analyzer according to claim 1, wherein the detector comprises a sample side chamber with a gas containing the measuring target component encapsulated therein, for allowing the first infrared rays to fall thereon, a balance side chamber for allowing the second infrared rays to fall thereon, and a flow sensor provided in a gas distribution path linking the sample side chamber with the balance side chamber.

4. An infrared gas analyzer according to claim 1, wherein the detector comprises a plurality of detectors of which measuring targets are gas components differing from each other.

5. An infrared gas analyzer according to claim 1, wherein the first and second infrared light sources are added with first and second optical sensors, respectively, for detecting abnormality of the respective light sources.

6. An infrared gas analyzer according to claim 1, wherein the measurement controller adjusts respective drive amounts of the second infrared light source at the time of a zero adjustment operation such that respective output of the detector becomes zero, and obtains the measurement output corresponding to respective concentrations of the measuring target component on the basis of magnitudes of the respective output of the detector at the time of a measuring operation.

7. An infrared gas analyzer according to claim 1, wherein the measurement controller adjusts respective drive amounts of the second infrared light source at the time of a zero adjustment operation such that respective output of the detector becomes zero, and adjusts the respective drive amounts of the second infrared light source at the time of a measuring operation as well such that the respective output of the detector becomes zero, thereby obtaining the measurement output corresponding to respective concentrations of the measuring target component on the basis of respective drive amount differentials at that point in time.

8. An infrared gas analyzer having a sample cell into which a sample gas is distributed, for detecting the concentration of a measuring target component of the sample gas by taking advantage of a variation in an absorption amount of infrared rays having passed through the sample cell, said infrared gas analyzer comprising:
   a first infrared light source for irradiating the sample cell with infrared rays;
   a second infrared light source having a response characteristic equal to that of the first infrared light source;
   a detector for detecting a difference between the first infrared rays emitted from the first infrared light source and passed through the sample cell, and second infrared rays emitted from the second infrared light source and falling directly on the detector, the detector having a plurality of the detectors which are individually provided with the second infrared light source;
   a light source drive controller for synchronously driving the first and second infrared light sources, respectively; and
   a measurement controller for providing the light source drive controller with instructions for respective drive amounts of the first and second infrared light sources while receiving an output signal from the detector, thereby generating a measurement output corresponding to the concentration of the measuring target component of the sample gas.

9. An infrared gas analyzer having a sample cell into which a sample gas is distributed, for detecting the concentration of a measuring target component of the sample gas by taking advantage of a variation in an absorption amount of infrared rays having passed through the sample cell, said infrared gas analyzer comprising:
   a first infrared light source for irradiating the sample cell with infrared rays;

a second infrared light source having a response characteristic equal to that of the first infrared light source;

a detector for detecting a difference between the first infrared rays emitted from the first infrared light source and passed through the sample cell, and second infrared rays emitted from the second infrared light source and falling directly on the detector;

a light source drive controller for synchronously driving, the first and second infrared light sources, respectively, the light source drive controller having a synchronous controller for generating a sync signal, first and second light source drivers, respectively, for turning ON/OFF drive signals to be supplied to the first and second infrared light sources, respectively, in response to the sync signal, and first and second drive signal detectors, respectively, for detecting magnitudes of the respective drive signals to be supplied to the first and second infrared light sources, respectively; and a measurement controller for providing the light source drive controller with instructions for respective drive amounts of the first and second infrared light sources while receiving an output signal from the detector, thereby generating a measurement output corresponding to the concentration of the measuring target component of the sample gas.

10. An infrared gas analyzer according to claim 9, wherein the light source drive controller has a synchronous controller for generating a sync signal, first and second light source drivers, respectively, for turning ON/OFF drive signals to be supplied to the first and second infrared light sources, respectively, in response to the sync signal, and first and second drive signal detectors, respectively, for detecting magnitudes of the respective drive signals to be supplied to the first and second infrared light sources, respectively, obtaining the measurement output corresponding to the respective concentrations of the measuring target component on the basis of a differential in output of the second drive signal detector at the time of the measuring operation.

11. An infrared gas analysis method of detecting the concentration of a measuring target component of a sample gas by taking advantage of a variation in an absorption amount of infrared rays having passed through a sample cell into which the sample gas is distributed, said method comprising the steps of:

irradiating the sample cell with first infrared rays emitted from a first infrared light source;

irradiating a balance side chamber with second infrared rays emitted from a second infrared light source having a response characteristic equal to that of the first infrared light source;

synchronously driving the first and second infrared light sources while detecting a difference between the first infrared rays emitted from the first infrared light source and passed through the sample cell, and the second infrared rays emitted from the second infrared light source and falling directly on a detector; and generating a measurement output corresponding to the concentration of the measuring target component of the sample gas.

12. An infrared gas analysis method according to claim 11, further comprising the step of synchronously turning ON/OFF the first and second infrared light sources in a predetermined cycle.

13. An infrared gas analysis according to claim 11, wherein the first and second infrared rays are photo-detected by a detector comprised of a sample side chamber with a gas containing the measuring target component encapsulated therein, for allowing the first infrared rays to fall thereon, a balance side chamber for allowing the second infrared rays to fall thereon, and a flow sensor provided in a gas distribution path linking the sample side chamber with the balance side chamber.

14. An infrared gas analysis method according to claim 13, wherein the detector comprises a plurality of detectors of which measuring targets are gas components differing from each other.

15. An infrared gas analysis method according to claim 11, wherein the first and second infrared light sources are added with first and second optical sensors, respectively, for detecting abnormality of the respective light sources.

16. An infrared gas analysis method according to claim 11, further comprising the step of adjusting respective drive amounts of the second infrared light source at the time of a zero adjustment operation such that a difference between the first infrared rays having passed through the sample cell, and the second infrared rays become zero, and obtaining the measurement output corresponding to respective concentrations of the measuring target component on the basis of the difference between the first infrared rays having passed through the sample cell, and the second infrared rays at the time of a measuring operation.

17. An infrared gas analysis method according to claim 11, further comprising the step of adjusting respective drive amounts of the second infrared light source at the time of a zero adjustment operation such that a difference between the first infrared rays having passed through the sample cell, and the second infrared rays become zero, and adjusting the respective drive amounts of the second infrared light source at the time of a measuring operation as well such that the difference between the first infrared rays having passed through the sample cell, and the second infrared rays becomes zero, thereby obtaining the measurement output corresponding to respective concentrations of the measuring target component on the basis of respective drive amount differentials.

18. An infrared gas analysis method of detecting the concentration of a measuring target component of a sample gas by taking advantage of a variation in an absorption amount of infrared rays having passed through a sample cell into which the sample gas is distributed, said method comprising the steps of:

irradiating the sample cell with first infrared rays emitted from a first infrared light source;

irradiating a balance side chamber with second infrared rays emitted from a second infrared light source having a response characteristic equal to that of the first infrared light source;

synchronously driving the first and second infrared light sources while detecting a difference between the first infrared rays emitted from the first infrared light source and passed through the sample cell, and second infrared rays emitted from the second infrared light source and falling directly on a detector comprises a plurality of detectors individually provided with the second infrared light source; and generating a measurement output corresponding to the concentration of the measuring target component of the sample gas.

19. An infrared gas analysis method of detecting the concentration of a measuring target component of a sample gas by taking advantage of a variation in an absorption amount of infrared rays having passed through a sample cell into which the sample gas is distributed, said method comprising the steps of:

irradiating the sample cell with first infrared rays emitted from a first infrared light source;

irradiating a balance side chamber with second infrared rays emitted from a second infrared light source having a response characteristic equal to that of the first infrared light source;

synchronously driving the first and second infrared light sources while detecting a difference between the first infrared rays emitted from the first infrared light source and passed through the sample cell, and second infrared rays emitted from the second infrared light source and falling directly on a detector;

generating a measurement output corresponding to the concentration of the measuring target component of the sample gas;

detecting magnitudes of respective drive signals to be supplied to the first and second infrared light sources, respectively; and feeding back the respective drive signals as detected to first and second light source drivers, respectively.

20. An infrared gas analysis method of detecting the concentration of a measuring target component of a sample gas by taking advantage of a variation of an absorption amount of infrared rays having passed through a sample cell into which the sample gas is distributed, said method comprising the steps of:

irradiating the sample cell with first infrared rays emitted from a first infrared light source;

irradiating a balance side chamber with second infrared rays emitted from a second infrared light source having a response characteristic equal to that of the first infrared light source;

synchronously driving the first and second infrared light sources while detecting a difference between the first infrared rays emitted from the first infrared light source and passed through the sample cell, and second infrared rays emitted from the second infrared light source and falling directly on a detector;

generating a measurement output corresponding to the concentration of the measuring target component of the sample gas;

detecting magnitudes of respective drive signals to be supplied to the first and second infrared light sources, respectively; and feeding back the respective drive signals as detected to first and second light source drivers, respectively, while obtaining the measurement output corresponding to the respective concentrations of the measuring target component on the basis of variation amounts of the respective drive signals at the second infrared light sources at the time of the measuring operation.

* * * * *